(12) United States Patent
Prakash (10) Patent No.: US 9,734,590 B2
(45) Date of Patent: Aug. 15, 2017

(54) PROCESS FOR MATCHING COLOR AND APPEARANCE OF COATINGS

(71) Applicant: AXALTA COATING SYSTEMS IP CO., LLC, Wilmington, DE (US)

(72) Inventor: Arun Prakash, West Chester, PA (US)

(73) Assignee: AXALTA COATING SYSTEMS IP CO., LLC, Wilmington, DE (US)

(*) Notice: Subject to any disclaimer, the term of this patent is extended or adjusted under 35 U.S.C. 154(b) by 149 days.

(21) Appl. No.: 14/769,840

(22) PCT Filed: Feb. 26, 2014

(86) PCT No.: PCT/US2014/018498
§ 371 (c)(1),
(2) Date: Aug. 24, 2015

(87) PCT Pub. No.: WO2014/134099
PCT Pub. Date: Sep. 4, 2014

(65) Prior Publication Data
US 2016/0005187 A1    Jan. 7, 2016

Related U.S. Application Data

(60) Provisional application No. 61/769,514, filed on Feb. 26, 2013.

(51) Int. Cl.
*G01J 3/46* (2006.01)
*G06T 7/40* (2017.01)
(Continued)

(52) U.S. Cl.
CPC .............. *G06T 7/408* (2013.01); *G01J 3/463* (2013.01); *G01J 3/504* (2013.01);
(Continued)

(58) Field of Classification Search
CPC ....... G06T 7/40; G01J 3/02; G01J 3/46; G01J 3/50; G01J 3/51; G01J 3/52; G01N 21/47; G01N 21/84
See application file for complete search history.

(56) References Cited

U.S. PATENT DOCUMENTS 6,952,265 B2 * 10/2005 Prakash ............. G01N 21/4738
356/445
8,065,314 B2 * 11/2011 Prakash .................... G01J 3/46
345/589
(Continued)

FOREIGN PATENT DOCUMENTS

WO    2013049792 A1    4/2013
WO    2013049796 A1    4/2013

OTHER PUBLICATIONS

ISA EPO, International Preliminary Report on Patentability issued in International Application No. PCT/US2014/018498, dated Sep. 11, 2015.
(Continued)

*Primary Examiner* — Abdullahi Nur
(74) *Attorney, Agent, or Firm* — Lorenz & Kopf, LLP (57) ABSTRACT

A process for producing a total match metric for matching color and appearance of a target coating and at least a specimen coating is provided. The total match metric (TMM) are produced based on color difference values ($\Delta E$) at three or more color viewing angles, sparkle difference values ($\Delta S$) at one or more sparkle viewing angles and flop difference value ($\Delta f$) between the target coating and the specimen coating using one or more linear functions, one or more non-linear functions, or a combination thereof. The total match metric can be used in producing matching coatings that match color and appearance of the target (Continued)

coating. The total match metric can be particularly useful for repair coating damages to vehicles.

24 Claims, 3 Drawing Sheets

(51) Int. Cl.
*G01J 3/50* (2006.01)
*G01N 21/47* (2006.01)
*G01N 21/84* (2006.01)
*G06T 7/90* (2017.01)
*G01J 1/44* (2006.01)

(52) U.S. Cl.
CPC ..... *G01N 21/4738* (2013.01); *G01N 21/8422* (2013.01); *G06T 7/90* (2017.01); *G01J 2001/4406* (2013.01); *G06T 2207/10024* (2013.01); *G06T 2207/30248* (2013.01)

(56) References Cited

U.S. PATENT DOCUMENTS

| 2005/0128484 | A1* | 6/2005 | Rodrigues | G01J 3/463 |
| | | | | 356/402 |
| 2006/0181707 | A1* | 8/2006 | Gibson | B01F 13/1055 |
| | | | | 356/402 |
| 2007/0292608 | A1 | 12/2007 | Rodrigues | |
| 2011/0246087 | A1* | 10/2011 | Prakash | G01J 3/463 |
| | | | | 702/23 |

OTHER PUBLICATIONS

ISA EPO, International Search Report and Written Opinion issued in International Application No. PCT/US2014/018498, dated Jun. 11, 2014.

* cited by examiner

PROCESS FOR MATCHING COLOR AND APPEARANCE OF COATINGS

CROSS-REFERENCE TO RELATED APPLICATION

This application is a U.S. National-Stage entry under 35 U.S.C. §371 based on International Application No. PCT/US2014/018498, filed Feb. 26, 2014, which was published in English under PCT Article 21(2) and which claims priority to U.S. Provisional Application No. 61/769,514, filed Feb. 26, 2013, all of which are incorporated herein by reference in their entirety.

TECHNICAL FIELD

The present disclosure is directed to a process for producing a match metric for matching color and appearance of a target coating and at least a specimen coating. The present disclosure is also directed to a process for producing a matching coating based on the match metric produced herein.

BACKGROUND

Surface coatings containing effect pigments, such as light absorbing pigments, light scattering pigments, and light interference pigments, and light reflecting pigments are commonly used. Flakes, such as metallic flakes, for example aluminum flakes, are examples of such effect pigments and are especially favored for the protection and decoration of automobile bodies, such as for example by reason of their imparting a differential light reflection effect, usually referred to as "flop", as well as flake appearance effects, which include flake size distribution and the sparkle imparted by the flake as well as the enhancement of depth perception in the coating. The flake containing coatings usually also contain other pigments or colorants, generally of a light absorbing rather than a light scattering type. These light absorbing pigments interact with effect pigments such as flakes to change the appearance effect of the coating. In general, visual coating appearance includes texture, sparkle, glitter or other visual effects of a coating. The visual appearance can vary when viewed from varying viewing angles, with varying illumination angles, or with varying illumination intensities.

For repairing a previously coated substrate, for example, of an automotive body, it is necessary to choose the correct colorants or colorant combinations to match the color of that coated substrate as well as the correct effect pigments such as metallic flakes to match the color and appearance of that coated substrate. Developments have been made to select colorants based on color measurement of a target coating. Selection of effect pigments, such as flakes, however, is traditionally done manually by an experienced shader, based on their expertise. Once the flakes have been selected, the flakes are added into a formulation algorithm producing one or more preliminary matching formulas. One or more test coatings are then prepared based on the preliminary matching formulas and sprayed on test panels, which are then visually compared to the target coating. If the appearance such as flop and/or sparkle match are deemed unsatisfactory, the shader adjusts the type and/or changes the amount of the flakes entered into the algorithm to get new color/flop matching formulas and the whole cycle is repeated until an adequate match is achieved in both color and appearance at all angles of illumination and viewing. This traditional approach, however, requires repeated spraying and visually comparing test panels with the target coating.

Accordingly, it is desirable to provide a process for matching both the color and appearance of the target coating. In addition, other objects, desirable features and characteristics will become apparent from the subsequent summary and detailed description, and the appended claims, taken in conjunction with the accompanying drawings and this background.

SUMMARY

In an exemplary embodiment, a process for producing a total match metric for matching color and appearance of a target coating and at least a specimen coating is provided. The process comprises the steps of:

A1) obtaining target color data of said target coating and specimen color data of said specimen coating produced from a specimen coating composition, wherein said target color data comprise target color values measured at three or more color viewing angles and said specimen color data comprise specimen color data values measured at said three or more color viewing angles;

A2) producing color difference values ($\Delta E$) at each of said color viewing angles based on said target color data and said specimen color data values at each of said color viewing angles;

A3) obtaining target sparkle data of said target coating and specimen sparkle data of said specimen coating, wherein said target sparkle data comprise target sparkle values measured at one or more sparkle viewing angles and said specimen sparkle data comprise specimen sparkle values measured at said one or more sparkle viewing angles;

A4) producing sparkle difference values ($\Delta S$) at each of said sparkle viewing angles based on said target sparkle data and said specimen sparkle data at each of said sparkle viewing angles;

A5) generating target flop data ($f^t$) of said target coating based on target lightness value derived from said target color data and specimen flop data ($f^s$) of said specimen coating based on specimen lightness value derived from said specimen color data;

A6) producing a flop difference value ($\Delta f$) based on said target flop data and said specimen flop data; and A7) producing said total match metric (TMM) of said target coating and said specimen coating based on said color difference values ($\Delta E$), said sparkle difference values ($\Delta S$) and said flop difference value ($\Delta f$).

In another exemplary embodiment, a process for producing a matching coating for matching color and appearance of a target coating coated over a substrate is provided. The process comprises the steps of:

B1) obtaining target coating identification data, target color data, target sparkle data and target flop data of said target coating, wherein said target color data comprise target color values measured at three or more color viewing angles, said target sparkle data comprise target sparkle values measured at one or more sparkle viewing angles, and said target flop data is generated based on target lightness value derived from said target color data;

B2) retrieving at least a specimen coating formulation from a color database based on said target coating identification data, said color database comprise coating formulations interrelated to and retrievable based on coating identification data;

B3) obtaining specimen color data, specimen sparkle data and specimen flop data associated with said specimen coating formulation, said specimen color data comprise specimen color data values measured at said three or more color viewing angles, said specimen sparkle data comprise specimen sparkle values measured at said one or more sparkle viewing angles, and said specimen flop data is generated based on specimen lightness value derived from said specimen color data, wherein:

said specimen color data, specimen sparkle data and specimen flop data are obtained by: (a) measuring at least one of said specimen color data and specimen sparkle data from a specimen coating produced based on said specimen coating formulation and generating said specimen flop data based on said specimen color data, (b) retrieving at least one of said specimen color data, specimen sparkle data and specimen flop data associated with said specimen coating formulation from said color database, or (c) a combination of (a) and (b);

B4) producing color difference values ($\Delta E$) at each of said color viewing angles based on said target color data and said specimen color data values at each of said color viewing angles;

B5) producing sparkle difference values ($\Delta S$) at each of said sparkle viewing angles based on said target sparkle data and said specimen sparkle data at each of said sparkle viewing angles;

B6) producing a flop difference value ($\Delta f$) based on said target flop data and said specimen flop data; and B7) producing a total match metric (TMM) of said target coating and said specimen coating based on said color difference values ($\Delta E$), said sparkle difference values ($\Delta S$) and said flop difference value ($\Delta f$).

In a further exemplar embodiment, a system for producing a total match metric for matching color and appearance of a target coating and at least a specimen coating is provided. The system comprises:

C1) a computing program product comprises computer executable codes stored on a computer readable storage medium, said computing program product causes a computing device to perform a computing process when in operation, said computing process comprises the steps of:

D1) receiving target coating identification data of said target coating when available, target color values and target sparkle values of said target coating and specimen color data values and specimen sparkle values of said specimen coating;

D2) generating target flop data of said target coating based on target lightness value derived from said target color data and specimen flop data of said specimen coating based on specimen lightness value derived from said specimen color data;

D3) producing color difference values ($\Delta E$) at each of said color viewing angles based on said target color data and said specimen color data values at each of said color viewing angles;

D4) producing sparkle difference values ($\Delta S$) at each of said sparkle viewing angles based on said target sparkle data and said specimen sparkle data at each of said sparkle viewing angles;

D5) producing a flop difference value ($\Delta f$) based on said target flop data and said specimen flop data;

D6) producing said total match metric (TMM) of said target coating and said specimen coating based on said color difference values ($\Delta E$), said sparkle difference values ($\Delta S$) and said flop difference value ($\Delta f$); and D7) outputting said total match metric as one or more output signals to an output device.

BRIEF DESCRIPTION OF DRAWINGS

The various embodiments will hereinafter be described in conjunction with the following drawing figures, wherein like numerals denote like elements, and wherein.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description.

The features and advantages of the present invention will be more readily understood, by those of ordinary skill in the art, from reading the following detailed description. It is to be appreciated that certain features of the invention, which are, for clarity, described above and below in the context of separate embodiments, may also be provided in combination in a single embodiment. Conversely, various features of the invention that are, for brevity, described in the context of a single embodiment, may also be provided separately or in any sub-combination. In addition, references in the singular may also include the plural (for example, "a" and "an" may refer to one, or one or more) unless the context specifically states otherwise.

The use of numerical values in the various ranges specified in this application, unless expressly indicated otherwise, are stated as approximations as though the minimum and maximum values within the stated ranges were both proceeded by the word "about." In this manner, slight variations above and below the stated ranges can be used to achieve substantially the same results as values within the ranges. Also, the disclosure of these ranges is intended as a continuous range including every value between the minimum and maximum values.

As used herein:

The term "dye" means a colorant or colorants that produce color or colors and is usually soluble in a coating composition.

The term "pigment" or "pigments" used herein refers to a colorant or colorants that produce color or colors and is usually not soluble in a coating composition. A pigment can be from natural and synthetic sources and made of organic or inorganic constituents. A pigment can also include metallic particles or flakes with specific or mixed shapes and dimensions.

The term "effect pigment" or "effect pigments" refers to pigments that produce special effects in a coating. Examples of effect pigments can include, but not limited to, light absorbing pigment, light scattering pigments, light interference pigments, and light reflecting pigments. Metallic flakes, for example aluminum flakes, can be examples of such effect pigments.

The term "gonioapparent flakes", "gonioapparent pigment" or "gonioapparent pigments" refers to pigment or pigments pertaining to change in color, appearance, or a combination thereof with change in illumination angle or viewing angle. Metallic flakes, such as aluminum flakes are examples of gonioapparent pigments. Interference pigments or pearlescent pigments can be further examples of gonioapparent pigments.

"Appearance" used herein refers to (1) the aspect of visual experience by which a coating is viewed or recognized; and (2) perception in which the spectral and geometric aspects of a coating is integrated with its illuminating and viewing environment. In general, appearance includes texture, sparkle, glitter, or other visual effects of a coating. Appearance usually varies with varying viewing angles or varying illumination angles.

The term "sparkle", "sparkles" or "sparkle effect" refers to the visual contrast between the appearance of highlights on particles of gonioapparent pigments and their immediate surroundings. Sparkle can be defined by, for example, ASTM E284-90 and other related standard methods.

The term "database" refers to a collection of related information that can be searched and retrieved. The database can be a searchable electronic numerical or textual document, a searchable PDF document, an Microsoft Excel® spreadsheet, an Microsoft Access® database (both supplied by Microsoft Corporation of Redmond, Wash.), an Oracle® database (supplied by Oracle Corporation of Redwood Shores, Calif.), or a Lynux database, each registered under their respective trademarks. The database can be a set of electronic documents, photographs, images, diagrams, or drawings, residing in a computer readable storage media that can be searched and retrieved. A database can be a single database or a set of related databases or a group of unrelated databases. "Related database" means that there is at least one common information element in the related databases that can be used to relate such databases. One example of the related databases can be Oracle® relational databases. In one example, color data comprising color values can be stored and retrieved from one or more databases. In another example, appearance characteristics, sparkle values and related measurements, coating formulations, vehicle data, or a combination thereof, can be stored and retrieved from one or more databases.

The term "color values" can refer to L,a,b color values, L*,a*,b* color values, XYZ color values, L,C,h color values, spectral reflectance values, light absorption (K) and scattering (S) values (also known as "K,S values"), or a combination thereof. Color values can also refer to other color values such as Hunter Lab color values, ANLAB color values, CIE LAB color values, CIE LUV color values, L*,C*,H* color values, or any other color values known to or developed by those skilled in the art, or a combination thereof.

The term "vehicle", "automotive", "automobile", "automotive vehicle", or "automobile vehicle" refers to an automobile such as car, van, mini van, bus, SUV (sports utility vehicle); truck; semi truck; tractor; motorcycle; trailer; ATV (all terrain vehicle); pickup truck; heavy duty mover, such as, bulldozer, mobile crane and earth mover; airplanes; boats; ships; and other modes of transport that are coated with coating compositions.

A computing device used herein can refer to a data processing chip, a desktop computer, a laptop computer, a pocket PC, a personal digital assistant (PDA), an handheld electronic processing device, a smart phone that combines the functionality of a PDA and a mobile phone, or any other electronic devices that can process information automatically. A computing device can be built into other electronic devices, such as a built-in data processing chip integrated into an imaging device, color measuring device, or an appearance measuring device such as a sparkle measuring device. A computing device can have one or more wired or wireless connections to a database, to another computing device, or a combination thereof. A computing device can be a client computer that communicates with a host computer in a multi-computer client-host system connected via a wired or wireless network including intranet and internet. A computing device can also be configured to be coupled with a data input or output device via wired or wireless connections. For example, a laptop computer can be operatively configured to receive color data and images through a wireless connection. A "portable computing device" includes a laptop computer, a pocket PC, a personal digital assistant (PDA), a handheld electronic processing device, a mobile phone, a smart phone that combines the functionality of a PDA and a mobile phone, a tablet computer, or any other electronic devices that can process information and data and can be carried by a person.

Wired connections include hardware couplings, splitters, connectors, cables or wires. Wireless connections and devices include, but not limited to, Wi-Fi device, Bluetooth device, wide area network (WAN) wireless device, local area network (LAN) device, infrared communication device, optical data transfer device, radio transmitter and optionally receiver, wireless phone, wireless phone adaptor card, or any other devices that can transmit signals in a wide range of radio frequency including visible or invisible optical wavelengths and electromagnetic wavelengths.

An imaging device can refer to a device that can capture images under a wide range of radio frequency including visible or invisible optical wavelengths and electromagnetic wavelengths. Examples of the imaging device include, but not limited to, a still film optical camera, an X-Ray camera, an infrared camera, a video camera, also collectively known as a low dynamic range (LDR) imaging device or a standard dynamic range (SDR) imaging device, and a high dynamic range (HDR) or wide dynamic range (WDR) imaging device such as those using two or more sensors having varying sensitivities. The HDR and the WDR imaging device can capture images at a greater dynamic range of luminance between the lightest and darkest areas of an image than typical standard imaging devices. A digital imager or digital imaging device refers to an imaging device captures images in digital signals. Examples of the digital imager include, but not limited to, a digital still camera, a digital video camera, a digital scanner, and a charge couple device (CCD) camera. An imaging device can capture images in black and white, gray scale, or various color levels. A digital imager is preferred in this invention. Images captured using a non-digital imaging device, such as a still photograph, can be converted into digital images using a digital scanner and can be also suitable for this invention. An imaging device can be used to measure appearance of a coating.

This disclosure is directed to a process for producing a total match metric for matching color and appearance of a target coating and at least a specimen coating. The process can comprise the steps of:

A1) obtaining target color data of the target coating and specimen color data of the specimen coating produced from a specimen coating composition, wherein the target color data comprise target color values measured at three or more color viewing angles and the specimen color data comprise specimen color values measured at the three or more color viewing angles;

A2) producing color difference values ($\Delta E$) at each of the color viewing angles based on the target color data and the specimen color data values at each of the color viewing angles;

A3) obtaining target sparkle data of the target coating and specimen sparkle data of the specimen coating, wherein the target sparkle data comprise target sparkle values measured at one or more sparkle viewing angles and the specimen sparkle data comprise specimen sparkle values measured at the one or more sparkle viewing angles;

A4) producing sparkle difference values ($\Delta S$) at each of the sparkle viewing angles based on the target sparkle data and the specimen sparkle data at each of the sparkle viewing angles;

A5) generating target flop data ($f^t$) of the target coating based on target lightness value derived from the target color data and specimen flop data ($f^s$) of the specimen coating based on specimen lightness value derived from the specimen color data;

A6) producing a flop difference value ($\Delta f$) based on the target flop data and the specimen flop data; and A7) producing the total match metric (TMM) of the target coating and the specimen coating based on the color difference values ($\Delta E$), the sparkle difference values ($\Delta S$) and the flop difference value ($\Delta f$).

The total match metric (TMM) of the target coating and the specimen coating can be produced from a computing device, wherein each of the steps can be programmed into computer executable codes. Any of the aforementioned computing devices can be suitable.

The total match metric (TMM) can be produced according to Formula (I):

$$TMM = f[\Delta E_{A1}, \Delta E_{A2}, \Delta E_{A3}, \Delta f, \Delta S_{P1}, \Delta S_{P2}] \quad (I);$$

wherein, $\Delta E_{A1}$ is a color difference value at color viewing angle $A_1$,
$\Delta E_{A2}$ is a color difference value at color viewing angle $A_2$,
$\Delta E_{A3}$ is a color difference value at color viewing angle $A_3$,
$\Delta f$ is the flop difference value based on the target flop data ($f^t$) and the specimen flop data ($f^s$);
$\Delta S_{P1}$ is a sparkle difference value at sparkle viewing angle $P_1$,
$\Delta S_{P2}$ is a sparkle difference value at sparkle viewing angle $P_2$;

the target flop data ($f^t$) is produced according to Formula (II-a):

$$f^t = g(L^t_{A1} - L^t_{A3})^{g'} / (L^t_{A2})^{g''} \quad (II\text{-}a);$$

the specimen flop data ($f^s$) is produced according to Formula (II-b):

$$f^s = g(L^s_{A1} - L^s_{A3})^{g'} / (L^s_{A2})^{g''} \quad (II\text{-}b);$$

g is a number in a range of from about 1 to about 6,
g' is a number in a range of from about 1 to about 3, and
g" is a number in a range of from about 0.1 to about 2,
$L^t_{A1}$ is the target lightness value derived from the target color data at the color viewing angle $A_1$,
$L^t_{A2}$ is the target lightness value derived from the target color data at the color viewing angle $A_2$,
$L^t_{A3}$ is the target lightness value derived from the target color data at the color viewing angle $A_3$,
$L^s_{A1}$ is the specimen lightness value derived from the specimen color data at the color viewing angle $A_1$,
$L^s_{A2}$ is a specimen lightness value derived from the specimen color data at the color viewing angle $A_2$,
$L^s_{A3}$ is a specimen lightness value derived from the specimen color data at the color viewing angle $A_3$;

the flop difference value ($\Delta f$) is produced according to Formula (III), (IV) or (V):

$$\Delta f = (f^t - f^s)/f^t, \text{ when } f^t < z \quad (III)$$

$$\Delta f = (f^s - z)/z, \text{ when } f^t \geq z \text{ and } f^s < z \quad (IV)$$

$$\Delta f = 0, \text{ when } f^t \geq z \text{ and } f^s \geq z \quad (V),$$

z is a number in a range of from about 12 to about 20;
the sparkle difference values are produced according to Formula (VI) and (VII):

$$\Delta S_{P1} = f(S^t_{P1}, S^s_{P1}) \quad (VI)$$

$$\Delta S_{P2} = f(S^t_{P2}, S^s_{P2}) \quad (VII),$$

$S^t_{P1}$ is the target sparkle data at the sparkle viewing angle $P_1$,
$S^s_{P1}$ is the specimen sparkle data at the sparkle viewing angle $P_1$,
$S^t_{P2}$ is the target sparkle data at the sparkle viewing angle $P_2$, and
$S^s_{P2}$ is the specimen sparkle data at the sparkle viewing angle $P_2$;

wherein the color viewing angles are aspecular angles $A_1$ in a range of from about 5° to about 25°, $A_2$ in a range of from about 30° to about 90° and $A_3$ in a range of from about 95° to about 165°; and the sparkle viewing angles are aspecular angles $P_1$ in a range of from about 5° to about 25° and $P_2$ in a range of from about 30° to about 90°.

Figure 1A:
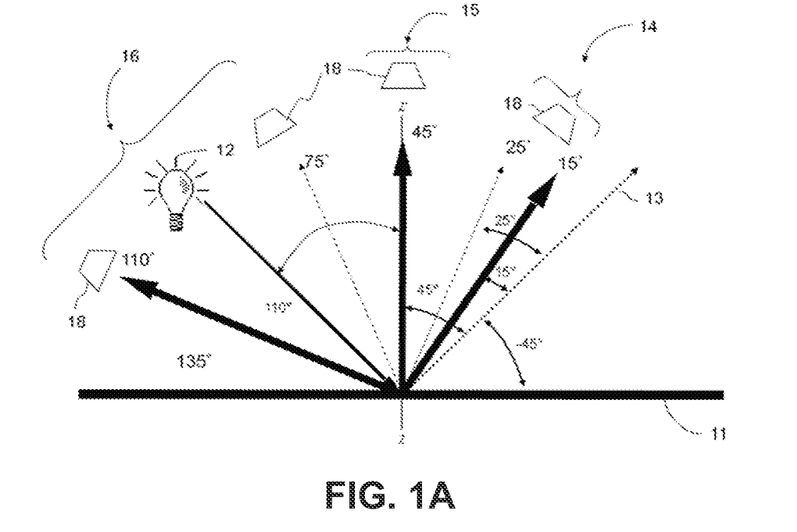
FIGS. 1A and 1B show examples of various illumination angles and viewing angles for a flat surface (A) or a curved surface (B).
Figure 1B:
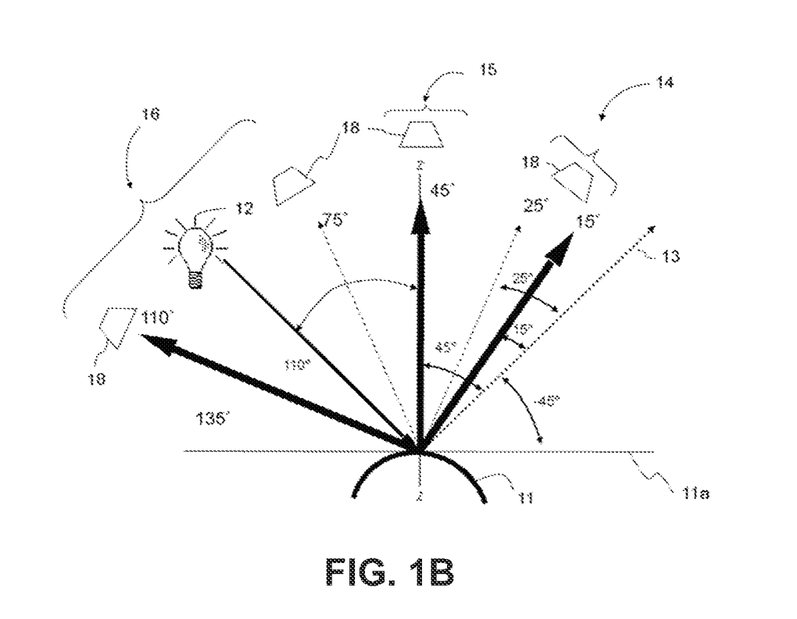

Color and appearance of a coating can vary in relation to illumination. An example of a standard procedure can include those described in ASTM E-2194. Briefly, when a coating (11) is illuminated by an illumination source (12), such as a light bulb or sun light, at an illumination angle as shown in FIG. 1A and FIG. 1B, a number of viewing angles can be used, such as, 1) near aspecular angles (14), that are color or sparkle viewing angles from about 15° to about 25° from the specular reflection (13) of the illumination; 2) mid aspecular angles (15), that are the viewing angles about 45° from the specular reflection (13) of the illumination; and 3) far aspecular angles (also known as flop angle) (16), that are the viewing angles from about 75° to about 110° from the specular reflection (13) of the illumination. In general, color appears to be slightly brighter at near aspecular angles and slightly darker at far aspecular angles. The illumination angle is the angle measured from the normal direction shown as Z-Z' (FIGS. 1A and 1B). The color can be viewed by a viewer or a detector (18) at the various viewing angles. Aspecular angles are the angles measured from the specular reflection (13) of the illumination.

Although specific view angles are specified above and can be preferred, viewing angles can include any viewing angles that are suitable for viewing the coating or detecting reflections of the coating. A viewing angle can be any angles, continuously or discretely, in a range of from 0° from the specular reflection (13) to the surface of the coating (11) on either side of the specular reflection (13) (FIG. 1A), or in a range of from 0° from the specular reflection (13) to the tangent (11a) of the surface of the coating (FIG. 1B). In one example, when the specular reflection (13) is at about 45° from the normal (Z-Z'), viewing angles can be any angles in the range of from about 0° to about −45° from the reflection, or from about 0° to about 135° from the reflection (FIG. 1A).

In another example, when the specular reflection (13) is at about 75° from the normal (Z-Z'), viewing angles can be any angles in the range of from about 0° to about −15° from the specular reflection, or from about 0° to about 165° from the specular reflection. Depending on the specular reflection (13), the range of viewing angles can be changed and determined by those skilled in the art.

Figure 2:
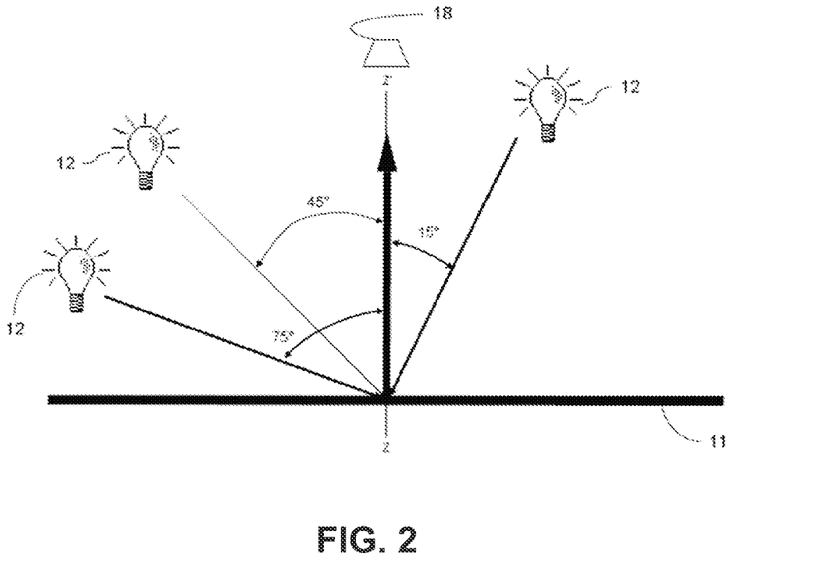
FIG. 2 shows examples of a fixed viewing angle and 3 illumination angles.

Another configuration is shown in FIG. 2 wherein a detector (18) can be fixed at the normal (Z-Z') facing towards the coating surface (11). One or more illumination sources (12) can be positioned to provide illumination at one or more illumination angles, such as at about 15°, about 45°, about 75°, or a combination thereof, from the normal (Z-Z') (FIG. 2).

The target color data can be selected from: measured target color values obtained by measuring a target coating produced from a target coating composition, retrieved target color values retrieved based on the target coating composition from a color database comprising color characteristics associated with coating compositions, predicted target color values obtained based on the target coating composition from a color predicting computing program product that predicts coating colors based on coating compositions, or a combination thereof. The measured target color characteristics can also be obtained from a coating that is produced from a coating composition identical to the target coating composition with all other ingredients except without the target effect pigment, with different size or amount of the target effect pigment, or with one or more different effect pigments. This can be particularly useful for producing matching coatings that can match a plurality of coatings having same or similar color, but different sparkle values. This can be particularly useful when the effect pigment has little or no effect on the color of the target coating composition.

The color values can be selected from L,a,b color values, L*,a*,b* color values, XYZ color values, L,C,h color values, spectral reflectance values, light absorption (K) and scattering (S) values (also known as "K,S values"), or a combination thereof. Other color values such as Hunter Lab color values, ANLAB color values, CIE LAB color values, CIE LUV color values, L*,C*,H* color values, any other color values known to or developed by those skilled in the art, or a combination thereof, can also be used. The color data values can be obtained at one or more color illumination angles, one or more color viewing angles, or a combination thereof. In one example, the color data values can be obtained at a viewing angle of about 15°, about 25°, about 45°, about 110°, or a combination thereof, the color viewing angle being an aspecular angle and can be measured with a color measuring device. The color measuring device can be a colorimeter, a spectrophotometer, or a goniospectrophotometer. Any suitable colorimeter or spectrophotometer, such as Model SP64 manufactured by X-Rite, Grandville, Mich. can be used. A goniospectrophotometer is also known as multi-angle spectrophotometer. Any suitable Goniospectrophotometers, such as Model MA68II from X-Rite, Grandville, Mich., or the ones provided by Murakami Color Research Laboratory, Tokyo, Japan, or by IsoColor Inc., Carlstadt, N.J., USA, can be used.

The color values can be converted from one form to another using methods known to or developed by those skilled in the art.

Sparkle values can be a function of sparkle intensity and sparkle area such as the function defined below:

$$S = f(S_i, S_a)$$

wherein, S, $S_i$ and $S_a$ are sparkle value, sparkling intensity, and sparkling area, respectively. One or more algorithms can be employed to define the function to calculate the S from $S_i$ and $S_a$. In one example, sparkle values can be obtained from commercial instruments, such as BYK-mac available from BYK-Gardner USA, Columbia, Md., USA.

The measured sparkle values can be obtained at one or more sparkle illumination angles, one or more sparkle viewing angles, or a combination thereof. In one example, measured sparkle values can be obtained at about 15° sparkle illumination angle. In another example, measured sparkle values can be obtained at about 45° sparkle illumination angle. In yet another example, measured sparkle values can be obtained at about 75° sparkle illumination angle. In a further example, measured sparkle values can be obtained at a combination of one or more of about 15°, about 25°, about 45°, and about 75° sparkle illumination angles. In yet one example, the measured sparkle values can be obtained at a sparkle viewing angle selected from about 15°, about 25°, about 45°, about 75°, or a combination thereof, the sparkle viewing angle being an aspecular angle.

Although specific illumination angles are specified above and can be preferred, illumination angles can include any angles that are suitable for illuminating the coating. The illumination angle can be any angles, continuously or discretely, in a range of from 0° from the normal (Z-Z') to 90° from the normal (Z-Z') of the surface of the coating (11) (FIG. 1A), or the tangent (11a) of the surface of the coating (FIG. 1B). In one example, the illumination angle can include any angles, continuously or discretely, in a range of from 0° to 90° from the normal (Z-Z') on either side of the normal.

Flop can be calculated based on lightness value derived from color data. The color data can comprise L,a,b color values measured at three or more color viewing angles. In one example, the color data can comprise L,a,b color values measured at color viewing angles of about 15°, about 45° and about 110°. The flop data (f) can be generated based on lightness value derived from the aforementioned color data at the color viewing angles of about 15°, about 45° and about 110° according to Formula (II):

$$f = 2.69 \cdot ((L_{15} - L_{110})^{1.11} / (L_{45})^{0.86}) \quad \text{(II)}.$$

The Formula (I) can be a linear function. In one example, the Formula (I) can be:

$$TMM = X_1 + X_2 + X_3 + X_4 + X_5 + X_6 \quad \text{(I-a)},$$

wherein, $X_1 = ((\Delta E_{A1})^n)/m$, n is a number in a range of from about 0.1 to about 2, m is a number in a range of from about 1 to about 5;

$X_2 = ((\Delta E_{A2})^{n'})/m'$, n' is a number in a range of from about 0.1 to about 2, m' is a number in a range of from about 1 to about 5;

$X_3 = (\Delta E_{A3})^{n''}/m''$, n" is a number in a range of from about 0.1 to about 2, m" is a number in a range of from about 1 to about 5;

$X_4 = ((a|(\Delta f - b)|)^q/p$, when $\Delta f \geq 0$; or $X_4 = ((a|(-\Delta f + b)|)^q/p$, when $\Delta f < 0$, a is a number in a range of from about 1 to about 5, b is a number in a range of from about 0.001 to about 0.1, p is a number in a range of from about 2 to about 20, q is a number in a range of from about 1 to about 5;

$X_5 = (|\Delta S_{P1}|)^r/S^t_{P1}$, when $\Delta S_{P1} \geq 0$; or $X_5 = c(|\Delta S_{P1}|)^r/S^t_{P1}$, when $\Delta S_{P1} < 0$; $S^t_{P1}$ is the target sparkle data at the sparkle viewing angle $P_1$, r is a number in a range of from about 1 to about 3, c is a number in a range of from about 1.1 to about 6; and $X_6=d(|\Delta S_{P2}|)^{r'}/S^t_{P2}$, when $\Delta S_{P2} \geq 0$; or $X_6=d'(|\Delta S_{P2}|)^{r'}/S^t_{P2}$, when $\Delta S_{P2}<0$; $S^t_{P2}$ is the target sparkle data at the sparkle viewing angle $P_2$, r' is a number in a range of from about 1 to about 3, d is a number in range of from about 1.10 to about 6, d' is a number in a range of from about 1.11 to about 8, and d'>d.

In another example, the Formula (I) can be:

$$TMM=X_1+X_2+X_3+X_4+X_5+X_6 \qquad (I\text{-}a),$$

wherein the color viewing angles are aspecular angles $A_1$ 15°, $A_2$ 45° and $A_3$ 110°; and the sparkle viewing angles are aspecular angles $P_1$ 15° and $P_2$ 45°; and wherein:

$X_1=((\Delta E_{15})^{0.5})/3$,
$X_2=((\Delta E_{45})^{0.75})/2$,
$X_3=(\Delta E_{110})/2$,
$X_4=((3|(\Delta f-0.0575)|)^4)/10$, when $\Delta f \geq 0$,
$X_4=((3|(-\Delta f+0.0575)|)^4)/10$, when $\Delta f<0$,
$X_5=(|\Delta S_{15}|)^2/S^t_{15}$, when $\Delta S_{P1} \geq 0$,
$X_5=1.5(|\Delta S_{15}|)^2/S^t_{15}$, when $\Delta S_{15}<0$,
$X_6=1.5(|\Delta S_{45}|)^2/S^t_{45}$, when $\Delta S_{45} \geq 0$, and
$X_6=2.25(|\Delta S_{45}|)^2/S^t_{45}$, when $\Delta S_{45}<0$.

In yet another example, the Formula (I) can be:

$$TMM=k(X'_1+X'_2+X'_3+X'_4+X'_5+X'_6) \qquad (I\text{-}b),$$

wherein:

k is a predetermined constant, $X'_1=\alpha(\Delta E_{A1})$, $\alpha$ is a number in a range of from about 0.1 to about 6,
$X'_2=\beta(\Delta E_{A2})$, $\beta$ is a number in a range of from about 0.1 to about 6,
$X'_3=\gamma(\Delta E_{A3})$, $\gamma$ is a number in a range of from about 0.1 to about 6,
$X'_4=((\lambda|(\Delta f)|)^\epsilon)/10$, $\lambda$ is a number in a range of from about 1 to about 6, $\epsilon$ is a number in a range of from about 1 to about 6,
$X'_5=|\Delta S_{P1}|/S^t_{P1}$, and
$X'_6=|\Delta S_{P2}|/S^t_{P2}$.

In another example, the Formula (I) can be:

$$TMM=k(X'_1+X'_2+X'_3+X'_4+X'_5+X'_6) \qquad (I\text{-}b),$$

wherein the color viewing angles are aspecular angles $A_1$ 15°, $A_2$ 45° and $A_3$ 110°; and the sparkle viewing angles are aspecular angles $P_1$ 15° and $P_2$ 45°; and wherein:

k is about 0.5,
$X'_1=0.5(\Delta E_{15})$,
$X'_2=0.75(\Delta E_{45})$,
$X'_3=\Delta E_{110}$,
$X'_4=((3|(\Delta f)|)^4)/10$,
$X'_5=|\Delta S_{15}|/S^t_{15}$, and
$X'_6=|\Delta S_{45}|/S^t_{45}$.

The Formula (I) can also be a non-linear function. In yet another example, the Formula (I) can be:

$$TMM=k_1(k_2(X''_1+k_3(X''_5)^{y_1}+(k_4(X''_2+k_5(X''_6))^{y_2}+k_6(X''_3)^{y_3}+X''_4) \qquad (I\text{-}c),$$

wherein:

$k_1$ is a number in a range of from about 0.1 to about 6,
$k_2$ is a number in a range of from about 0.1 to about 3,
$k_3$ is a number in a range of from about 1 to about 20,
$k_4$ is a number in a range of from about 0.1 to about 3,
$k_5$ is a number in a range of from about 0.1 to about 3,
$k_6$ is a number in a range of from about 0.1 to about 3,
$y_1$ is a number in a range of from about 0.1 to about 3,
$y_2$ is a number in a range of from about 1 to about 6,
$y_3$ is a number in a range of from about 1 to about 6, $X''_1=\alpha(\Delta E_{A1})$, $\alpha$ is a number in a range of from about 0.1 to about 6,
$X''_2=\beta(\Delta E_{A2})$, $\beta$ is a number in a range of from about 0.1 to about 6,
$X''_3=\gamma(\Delta E_{A3})$, $\gamma$ is a number in a range of from about 0.1 to about 6,
$X''_4=((\lambda|(\Delta f)|)^\epsilon)/10$, $\lambda$ is a number in a range of from about 1 to about 6, $\epsilon$ is a number in a range of from about 1 to about 6,
$X''_5=|\Delta S_{P1}|/S^t_{P1}$, and
$X''_6=|\Delta S_{P2}|/S^t_{P2}$.

In another example, TMM can be produced according to the Formula (I-c) with predetermined constants:

$$TMM=0.8(0.15(X''_1+12(X''_5)^{0.75}+(0.5(X''_2+12(X''_6))^{1.25}+0.65(X''_3)^{1.75}+X''_4)$$

wherein the color viewing angles are aspecular angles $A_1$ 15°, $A_2$ 45° and $A_3$ 110°; and the sparkle viewing angles are aspecular angles $P_1$ 15° and $P_2$ 45°; and wherein $X''_1=\Delta E_{15}$,
$X''_2=\Delta E_{45}$,
$X''_3=\Delta E_{110}$,
$X''_4=((3|(\Delta f)|)^4)/10$,
$X''_5=|\Delta S_{15}|/S^t_{15}$, and
$X''_6=|\Delta S_{45}|/S^t_{45}$.

The process can further comprise the steps of:

A8) producing at least a target image of the target coating, the target image comprises target display R,G,B values based on the target color data, the target sparkle data and the target flop data;

A9) producing at least a specimen image of the specimen coating, the specimen image comprises specimen display R,G,B values based on the specimen color data, the specimen sparkle data and the specimen flop data;

A10) displaying the target image, the specimen image, or a combination thereof, on a display device based on the target display R,G,B values and the specimen display R,G,B values.

One or more target images can be generated. In one example, one or more target images representing the target coating at one or more viewing angles can be generated.

The target image, the specimen image, or a combination thereof, can be produced and displayed based on one or more illumination angles, one or more viewing angles, or a combination thereof. Images representing multiple viewing angles can be referred to as realistic matching images. The target image, the specimen image, or a combination thereof, can be produced and displayed as realistic images. Methods for generating images or realistic images of coating color and appearance based on coating formulas and color and appearance characteristics are described in U.S. Pat. No. 7,639,255, filed on Oct. 27, 2006, which is incorporated by reference in their entirety. In brief, the images are produced by converting color data such as the L,a,b, or L*,a*,b*, color values at at least three angles to corresponding XYZ color values, calculating a range of aspecular angles required for display, and calculating corresponding R, G, B values from the corresponding XYZ color values and the angles for display. The target image, the specimen image, or a combination thereof, can be displayed as high dynamic range (HDR) images. The HDR images can be generated using high dynamic range (HDR) rendering. In one example the target image, the specimen image, or a combination thereof, can be generated into a plurality of standard images at various ranges and then merged together to form one or more HDR images for better display of details at various ranges. The images can be generated using bidirectional reflectance distribution function (BRDF). One example of a method for generating image using BRDF is disclosed in U.S. Pat. Nos. 8,374,831, 8,103,491 and 7,991,596, which are incorporated by reference in their entirety.

The display device can be a computer monitor, a projector, a TV screen, a personal digital assistant (PDA) device, a cell phone, a smart phone that combines PDA and cell phone, an iPod, an iPod/MP Player, a flexible thin film display, a high dynamic range (HDR) image display device, a low dynamic range (LDR), a standard dynamic range (SDR) display device, or any other display devices that can display information or images based on digital signals. The display device can also be a printing device that prints, based on digital signals, information or image onto papers, plastics, textiles, or any other surfaces that are suitable for printing the information or images onto. The display device can also be a multi-functional display/input/output device, such as a touch screen. The HDR target image can be displayed on a HDR image display device, a non-HDR image display device mentioned herein, or a combination thereof. The non-HDR image display device can be any of the display devices such as those standard display devices, or low dynamic range (LDR) or standard dynamic range (SDR) display devices. The HDR image needs to be modified to display on a non-HDR image display device. Since the sparkles can have very high intensity, they can be difficult to display together with color characteristics in a same image. The HDR image can be used to improve the display of sparkles and colors.

The process disclosed herein can further comprise the steps of:

A11) producing a matching coating composition for matching color and appearance of the target coating, wherein the matching coating composition is based on the specimen coating composition when the total match metric (TMM) is within a predetermined matching tolerance range for matching the target coating and the specimen coating, and optionally producing a matching coating matching color and appearance of the target coating using the matching coating composition.

The process disclosed herein can further comprise the steps of:

A12) producing at least one modified coating formulation based on the total match metric (TMM) for a modified coating, when the total match metric (TMM) is outside a predetermined matching tolerance range for match the target coating and the specimen coating;

A13) producing a modified coating based on the modified coating formulation;

A14) repeating the steps A1)-A7) to produce a modified total match metric of the target coating and the modified coating;

A15) repeating the steps A12)-A15) until the modified total match metric is within the predetermined matching tolerance range;

A16) optionally, producing a matching coating composition for matching color and appearance of the target coating, wherein the matching coating composition is based on the modified coating formulation having the modified total match metric within the predetermined matching tolerance range; and A17) optionally, producing a matching coating matching color and appearance of the target coating using the matching coating composition.

The target coating can be coated over a substrate. The substrate can be a vehicle, a vehicle part, or a combination thereof.

This disclosure is directed to a process for producing a matching coating for matching color and appearance of a target coating coated over a substrate. The process can comprise the steps of:

B1) obtaining target coating identification data, target color data, target sparkle data and target flop data of the target coating, wherein the target color data comprise target color values measured at three or more color viewing angles, the target sparkle data comprise target sparkle values measured at one or more sparkle viewing angles, and the target flop data is generated based on target lightness value derived from the target color data;

B2) retrieving at least a specimen coating formulation from a color database based on the target coating identification data, the color database comprise coating formulations interrelated to and retrievable based on coating identification data;

B3) obtaining specimen color data, specimen sparkle data and specimen flop data associated with the specimen coating formulation, the specimen color data comprise specimen color values measured at the three or more color viewing angles, the specimen sparkle data comprise specimen sparkle values measured at the one or more sparkle viewing angles, and the specimen flop data is generated based on specimen lightness value derived from the specimen color data, wherein:

the specimen color data, specimen sparkle data and specimen flop data are obtained by: (a) measuring at least one of the specimen color data and specimen sparkle data from a specimen coating produced based on the specimen coating formulation and generating the specimen flop data based on the specimen color data, (b) retrieving at least one of the specimen color data, specimen sparkle data and specimen flop data associated with the specimen coating formulation from the color database, or (c) a combination of (a) and (b);

B4) producing color difference values ($\Delta E$) at each of the color viewing angles based on the target color data and the specimen color data values at each of the color viewing angles;

B5) producing sparkle difference values ($\Delta S$) at each of the sparkle viewing angles based on the target sparkle data and the specimen sparkle data at each of the sparkle viewing angles;

B6) producing a flop difference value ($\Delta f$) based on the target flop data and the specimen flop data; and B7) producing a total match metric (TMM) of the target coating and the specimen coating based on the color difference values ($\Delta E$), the sparkle difference values ($\Delta S$) and the flop difference value ($\Delta f$).

The substrate can be a vehicle, a vehicle part, or a combination thereof. The target coating identification data can be selected from a name or a code of the target coating, color values of the target coating measured at one or more viewing angles, a vehicle identification number (VIN) of the vehicle, a part of the VIN, make of the vehicle, model and model year of the vehicle, manufacturing site information of the vehicle, manufacturer's paint code of the vehicle, or a combination thereof.

The total match metric (TMM) can be produced according to Formula (I):

$$\mathrm{TMM}=f[\Delta E_{A1},\Delta E_{A2},\Delta E_{A3},\Delta f,\Delta S_{P1},\Delta S_{P2}] \quad (\mathrm{I})$$

wherein, $\Delta E_{A1}$ is a color difference value at color viewing angle $A_1$,
$\Delta E_{A2}$ is a color difference value at color viewing angle $A_2$,
$\Delta E_{A3}$ is a color difference value at color viewing angle $A_3$, Δf is the flop difference value based on the target flop data (f$^t$) and the specimen flop data (f$^s$);

ΔS$_{P1}$ is a sparkle difference value at sparkle viewing angle P$_1$,

ΔS$_{P2}$ is a sparkle difference value at sparkle viewing angle P$_2$;

the target flop data (f$^t$) is produced according to Formula (II-a):

$$f^t = g(L^t_{A1} - L^t_{A3})^{g'}/(L^t_{A2})^{g''} \qquad \text{(II-a)}$$

the specimen flop data (f$^s$) is produced according to Formula (II-b):

$$f^s = g(L^s_{A1} - L^s_{A3})^{g'}/(L^s_{A2})^{g''} \qquad \text{(II-b)}$$

g is a number in a range of from about 1 to about 6, g' is a number in arrange of from about 1 to about 3, and g'' is a number in a range of from about 0.1 to about 2, L$^t_{A1}$ is the target lightness value derived from the target color data at the color viewing angle A$_1$, L$^t_{A2}$ is the target lightness value derived from the target color data at the color viewing angle A$_2$, L$^t_{A3}$ is the target lightness value derived from the target color data at the color viewing angle A$_3$, L$^s_{A1}$ is the specimen lightness value derived from the specimen color data at the color viewing angle A$_1$, L$^s_{A2}$ is a specimen lightness value derived from the specimen color data at the color viewing angle A$_2$, L$^s_{A3}$ is a specimen lightness value derived from the specimen color data at the color viewing angle A$_3$;

the flop difference value (Δf) is produced according to Formula (III), (IV) or (V):

$$\Delta f = (f^s - f^t)/f^t, \text{ when } f^s < z \qquad \text{(III)}$$

$$\Delta f = (f^s - z)/z, \text{ when } f^t \geq z \text{ and } f^s < z \qquad \text{(IV)}$$

$$\Delta f = 0, \text{ when } f^t \geq z \text{ and } f^s \geq z \qquad \text{(V)},$$

z is a number in a range of from about 12 to about 20;

the sparkle difference values are produced according to Formula (VI) and (VII):

$$\Delta S_{P1} = (S^t_{P1} - S^s_{P1}) \qquad \text{(VI)}$$

$$\Delta S_{P2} = (S^t_{P2} - S^s_{P2}) \qquad \text{(VII)}$$

S$^t_{P1}$ is the target sparkle data at the sparkle viewing angle P$_1$,

S$^s_{P1}$ is the specimen sparkle data at the sparkle viewing angle P$_1$,

S$^t_{P2}$ is the target sparkle data at the sparkle viewing angle P$_2$, and

S$^s_{P2}$ is the specimen sparkle data at the sparkle viewing angle P$_2$;

wherein the color viewing angles are aspecular angles A$_1$ in a range of from about 5° to about 25°, A$_2$ in a range of from about 30° to about 90° and A$_3$ in a range of from about 95° to about 165°; and the sparkle viewing angles are aspecular angles P$_1$ in a range of from about 5° to about 25° and P$_2$ in a range of from about 30° to about 90°.

In one example, the Formula (I) can be:

$$\text{TMM} = X_1 + X_2 + X_3 + X_4 + X_5 + X_6 \qquad \text{(I-a)}$$

wherein,

X$_1$ = ((ΔE$_{A1}$)$^n$)/m, n is a number in a range of from about 0.1 to about 2, m is a number in a range of from about 1 to about 5;

X$_2$ = ((ΔE$_{A2}$)$^{n'}$)/m', n' is a number in a range of from about 0.1 to about 2, m' is a number in a range of from about 1 to about 5;

X$_3$ = (ΔE$_{A3}$)$^{n''}$/m'', n'' is a number in a range of from about 0.1 to about 2, m'' is a number in a range of from about 1 to about 5;

X$_4$ = ((a|(Δf−b)|)$^q$/p, when Δf ≥ 0; or X$_4$ = ((a|(−Δf+b)|)$^q$/p, when Δf < 0, a is a number in a range of from about 1 to about 5, b is a number in a range of from about 0.001 to about 0.1, p is a number in a range of from about 2 to about 20, q is a number in a range of from about 1 to about 5;

X$_5$ = (|ΔS$_{P1}$|)$^r$/S$^t_{P1}$, when ΔS$_{P1}$ ≥ 0; or X$_5$ = c(|ΔS$_{P1}$|)$^r$/S$^t_{P1}$, when ΔS$_{P1}$ < 0; S$^t_{P1}$ is the target sparkle data at the sparkle viewing angle P$_1$, r is a number in a range of from about 1 to about 3, c is a number in a range of from about 1.1 to about 6; and X$_6$ = d(|ΔS$_{P2}$|)$^{r'}$/S$^t_{P2}$, when ΔS$_{P2}$ ≥ 0; or X$_6$ = d'(|ΔS$_{P2}$|)$^{r'}$/S$^t_{P2}$, when ΔS$_{P2}$ < 0; S$^t_{P2}$ is the target sparkle data at the sparkle viewing angle P$_2$, r' is a number in a range of from about 1 to about 3, d is a number in range of from about 1.10 to about 6, d' is a number in a range of from about 1.11 to about 8, and d' > d.

In another example, the Formula (I) can be:

$$\text{TMM} = k(X'_1 + X'_2 + X'_3 + X'_4 + X'_5 + X'_6) \qquad \text{(I-b)}$$

wherein:

k is a predetermined constant,

X'$_1$ = α(ΔE$_{A1}$), α is a number in a range of from about 0.1 to about 6,

X'$_2$ = β(ΔE$_{A2}$), β is a number in a range of from about 0.1 to about 6,

X'$_3$ = γ(ΔE$_{A3}$), γ is a number in a range of from about 0.1 to about 6,

X'$_4$ = ((λ|(Δf)|)$^ε$/10, λ is a number in a range of from about 1 to about 6, ε is a number in a range of from about 1 to about 6, X'$_5$ = |ΔSp$_1$|/S$^t_{P1}$, and X'$_6$ = |ΔS$_{P2}$|/S$^t_{P2}$.

In the process disclosed here, the Formula (I) can also be:

$$\text{TMM} = k_1(k_2(X''_1 + k_3(X''_5)^{y_1} + (k_4(X''_2 + k_5(X''_6)^{y_2} + k_6(X''_3)^{y_3} + X''_4) \qquad \text{(I-c)}$$

wherein:

k$_1$ is a number in a range of from about 0.1 to about 6, k$_2$ is a number in a range of from about 0.1 to about 3, k$_3$ is a number in a range of from about 1 to about 20, k$_4$ is a number in a range of from about 0.1 to about 3, k$_5$ is a number in a range of from about 0.1 to about 3, k$_6$ is a number in a range of from about 0.1 to about 3, y$_1$ is a number in a range of from about 0.1 to about 3, y$_2$ is a number in a range of from about 1 to about 6, y$_3$ is a number in a range of from about 1 to about 6, X''$_1$ = α(ΔE$_{A1}$), α is a number in a range of from about 0.1 to about 6, X''$_2$ = β(ΔE$_{A2}$), β is a number in a range of from about 0.1 to about 6, X''$_3$ = γ(ΔE$_{A3}$), γ is a number in a range of from about 0.1 to about 6, X''$_4$ = ((λ|(Δf)|)$^ε$/10, λ is a number in a range of from about 1 to about 6, ε is a number in a range of from about 1 to about 6, X''$_5$ = |ΔS$_{P1}$|/S$^t_{P1}$, and X''$_6$ = |ΔS$_{P2}$|/S$^t_{P2}$.

The process disclosed herein can further comprise the steps of:

B8) producing at least a target image of the target coating, the target image comprises target display R,G,B values based on the target color data, the target sparkle data and the target flop data;

B9) producing at least a specimen image of the specimen coating, the specimen image comprises specimen display R,G,B values based on the specimen color data, the specimen sparkle data and the specimen flop data;

B10) displaying the target image, the specimen image, or a combination thereof, on a display device based on the target display R,G,B values and the specimen display R,G,B values.

The target images and the specimen images can be produced and displayed as described above. Any of the aforementioned display devices can be suitable.

The process can further comprise the steps of:

B11) producing a matching coating composition for matching color and appearance of the target coating, wherein the matching coating composition is based on the specimen coating composition when the total match metric (TMM) is within a predetermined matching tolerance range for matching the target coating and the specimen coating, and optionally producing the matching coating matching color and appearance of the target coating using the matching coating composition.

The process can further comprise the steps of:

B12) producing at least one modified coating formulation based on the total match metric (TMM) for a modified coating, when the total match metric (TMM) is outside a predetermined matching tolerance range for match the target coating and the specimen coating;

B13) producing a modified coating based on the modified coating formulation;

B14) repeating the steps B3)-B7) to produce a modified total match metric of the target coating and the modified coating;

B15) repeating the steps B12)-B15) until the modified total match metric is within the predetermined matching tolerance range; and B16) producing a matching coating composition for matching color and appearance of the target coating, wherein the matching coating composition is based on the modified coating formulation having the modified total match metric within the predetermined matching tolerance range; and B17) optionally, producing the matching coating matching color and appearance of the target coating using the matching coating composition.

This disclosure is further directed to a system for producing a total match metric for matching color and appearance of a target coating and at least a specimen coating. The system can comprise:

C1) a computing program product comprises computer executable codes stored on a computer readable storage medium, the computing program product causes a computing device to perform a computing process when in operation, the computing process comprises the steps of:

D1) receiving target coating identification data of the target coating when available, target color values and target sparkle values of the target coating and specimen color values and specimen sparkle values of the specimen coating;

D2) generating target flop data of the target coating based on target lightness value derived from the target color data and specimen flop data of the specimen coating based on specimen lightness value derived from the specimen color data;

D3) producing color difference values ($\Delta E$) at each of the color viewing angles based on the target color data and the specimen color data values at each of the color viewing angles;

D4) producing sparkle difference values ($\Delta S$) at each of the sparkle viewing angles based on the target sparkle data and the specimen sparkle data at each of the sparkle viewing angles;

D5) producing a flop difference value ($\Delta f$) based on the target flop data and the specimen flop data;

D6) producing the total match metric (TMM) of the target coating and the specimen coating based on the color difference values ($\Delta E$), the sparkle difference values ($\Delta S$) and the flop difference value ($\Delta f$); and D7) outputting the total match metric as one or more output signals to an output device.

Figure 3:
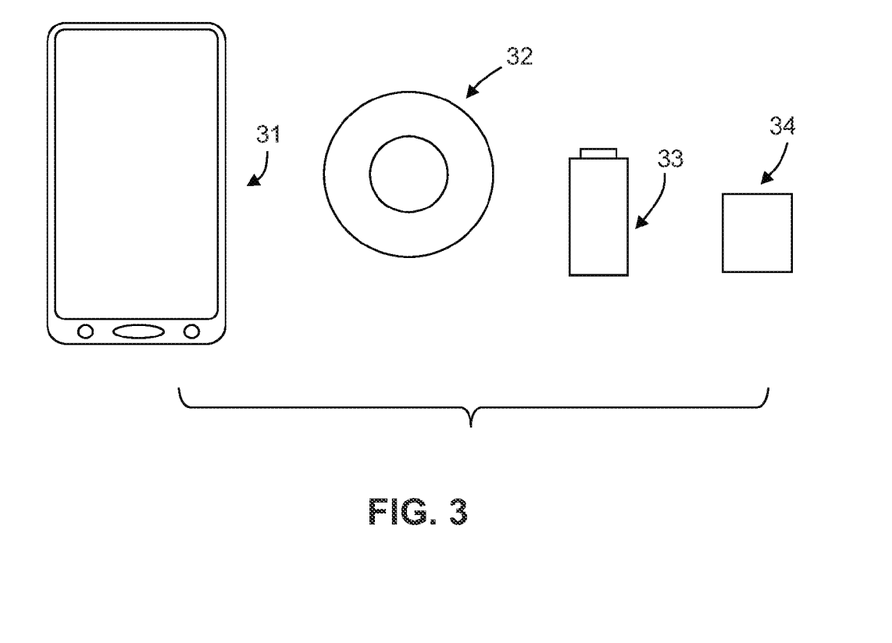
FIG. 3 shows examples of computing program products.

The computer readable storage medium can be one or more digital data storage media, such as a smart phone or PDA (personal digital assistant) (31), a compact disc or DVD (32), a flash memory device such as a USB drive (33) or SD card (34), or a combination thereof (FIG. 3). Any other computer readable storage medium known to or developed by those skilled in the art can be suitable.

The system of this disclosure can further comprise:

C2) a color measuring device for producing the target color values of the target coating at three or more color viewing angles and the specimen color values of the specimen coating at the three or more color viewing angles;

C3) a sparkle measuring device for producing the target sparkle values of the target coating at one or more sparkle viewing angles and the specimen sparkle values of the specimen coating at the one or more sparkle viewing angles;

C4) the computing device functionally in communication with the color measuring device and the sparkle measuring device, when in operation; and C5) the output device functionally in communication with the computing device, when in operation.

The system of this disclosure can further comprise:

C6) a color database (44) functionally in communication with the computing device, the color database comprise coating formulations interrelated to and retrievable based on names or codes of coatings, color characteristics of coatings, appearance characteristics of coatings, vehicle identification numbers (VINs) of vehicles, parts of the VINs, makes of vehicles, models and model years of vehicles, manufacturing sites information of vehicles, manufacturer's paint codes of vehicles, or a combination thereof.

The output device can be selected from a digital display device, a printer, a digital data storage device, a database, a second computing device, or a combination thereof. Typically, the computing device can comprise a display device as part of the output device.

Figure 4A:
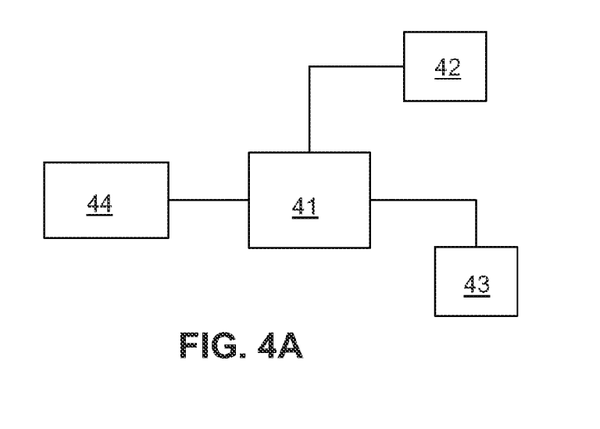
FIGS. 4A through 4C show examples of the system.
Figure 4B:
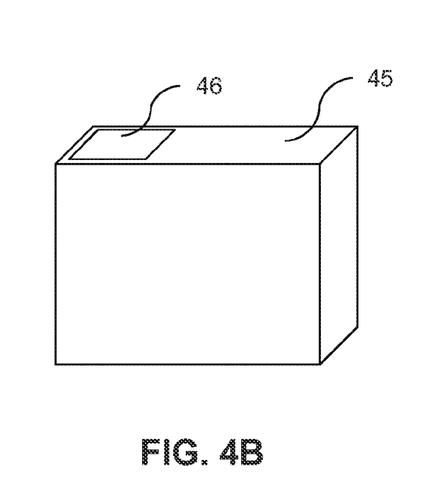
Figure 4C:
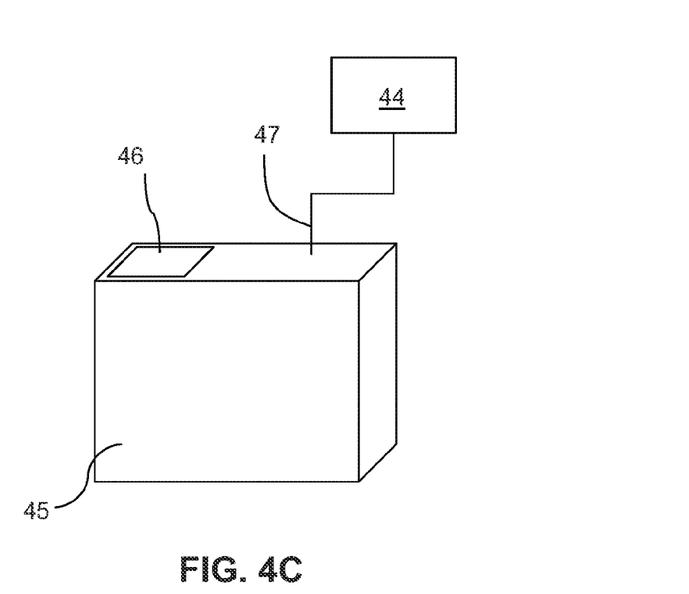

In one example, the system can comprise a computing device (41) that can have the computing program product installed thereon or accessed therefrom and can be functionally coupled to a sparkle measuring device (42), a sparkle measuring device (43) and a database (44) such as the color database (FIG. 4A). In another example, the system can be a portable device (45) that can comprise one or more functionally coupled components selected from a computing device that can have the computing program product installed thereon or accessed therefrom, a sparkle measuring device, a sparkle measuring device, a database such as the color database, a display device (46), or a combination thereof (FIG. 4B). In yet another example, the system can be a portable device (45) that can comprise one or more functionally coupled components selected from a computing device that can have the computing program product installed thereon or accessed therefrom, a sparkle measuring device, a sparkle measuring device, a display device (46), or a combination thereof, and a database (44) such as the color database functionally coupled to the portable device via wired or wireless connections (47) (FIG. 4C). In yet another example, the computing device of any of the aforementioned portable devices can have wired or wireless connections to a another computing device, a host computer, networks such as internet or intranet, additional devices selected from an input device, such as a keyboard, a digital data reader, an optical reader such as barcode reader, a data input portal, or a combination thereof; a gloss meter; an imaging device; a surface measurement devices; or a combination thereof. Any of the aforementioned wired or wireless connections can be suitable.

The step for producing the total match metric (TMM) of the target coating and the specimen coating based on the color difference values ($\Delta E$), the sparkle difference values ($\Delta S$) and the flop difference value ($\Delta f$) means that at least the $\Delta E$, the $\Delta S$ and the $\Delta f$ are required. Further coating parameters, differences of the parameters, or a combination thereof can also be included in producing the TMM and can include, but not limited to, such as $\Delta E^*_{ab}$ based on CIE76, $\Delta E^*_{94}$ based on CIE 94, $\Delta E^*_{00}$ based on CIEDE2000, or any other color difference values known to or developed by those skilled in the art; texture of coatings; roughness of coatings; gloss of coatings; or a combination thereof. Texture of coatings can be measured, for example, with an imaging device as described in U.S. Pat. No. 8,270,699. Roughness of coatings can be measured, for example with an optical profiler, a stylus profiler, a cantilever profiler, an imaging device, or a combination thereof. Gloss of coatings can be measured, for example, with a gloss meter. In one further example, TMM can be produced based on $\Delta E$, $\Delta S$, $\Delta f$ and a texture difference value ($\Delta T$) between the target coating and the specimen coating. In yet another example, TMM can be produced based on $\Delta E$, $\Delta S$, $\Delta f$ and a roughness difference value ($\Delta R$) between the target coating and the specimen coating. In yet another example, TMM can be produced based on $\Delta E$, $\Delta S$, $\Delta f$ and a gloss difference value ($\Delta G$) between the target coating and the specimen coating. In yet another example, TMM can be produced based on $\Delta E$, $\Delta S$, $\Delta f$ and a combination of $\Delta R$, $\Delta T$ and $\Delta G$.

In one example, TMM can be produced according to Formula (I-1):

$$\mathrm{TMM}=f[\Delta E_{A1},\Delta E_{A2},\Delta E_{A3},\Delta f,\Delta S_{P1},\Delta S_{P2},\Delta R] \quad (I\text{-}1).$$

In another example, TMM can be produced according to Formula (I-2):

$$\mathrm{TMM}=f[\Delta E_{A1},\Delta E_{A2},\Delta E_{A3},\Delta f,\Delta S_{P1},\Delta S_{P2},\Delta R,\Delta T] \quad (I\text{-}2).$$

In yet a further example, TMM can be produced according to the Formula (I-3):

$$\mathrm{TMM}=f[\Delta E_{A1},\Delta E_{A2},\Delta E_{A3},\Delta f,\Delta S_{P1},\Delta S_{P2},\Delta R,\Delta T,\Delta G] \quad (I\text{-}3).$$

Any of the aforementioned Formulas can comprise linear function, non-linear function, or a combination thereof.

The process and system of this disclosure can provide a single quantitative metric (TMM) between the target coating and one or more specimen coatings for easy color and appearance match. The process and system can be particularly useful for ranking a plurality of specimen coatings with a single metric.

Although vehicle and vehicle coating are specifically described, this disclosure can also be used for other coated articles or article without coating wherein color or appearance of the articles can be identified by article identification data, such as catalog numbers or color codes. Some examples of such coated articles include, but not limited to: home appliances, such as refrigerator, washing machine, dishwasher, microwave ovens, cooking and baking ovens; electronic appliances, such as television sets, computers, electronic game sets, audio and video equipments; recreational equipments, such as bicycles, ski equipments, all terrain vehicles; and home or office furniture, such as tables, file cabinets. Examples of articles without coating that have color and appearance include, but not limited to, engineering polymers, injection molding plastics or polymers, or other synthetic materials such as Corian® available from DuPont, wherein Corian® is a registered trademark of DuPont. Selection of matching formulas for repairing the coatings of the articles or articles without coating can be performed according to the method of this disclosure.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

A target coating was a car part from a 2005 Pontiac Grand AM painted with a paint color code 817K63 and 3 specimen coatings were produced from Chromabase® quality paint formulations, avaibale from DuPont™ under registered trademarks/trademarks of E.I du Pont de Nemours and Company, Wilmington, Del., USA, developed for matching field variations of the target coating sprayed onto test panels. Both the target coating and the specimen coatings were metallic with aluminum flakes.

Color values including L,a,b color values were measured with Byk-mac purchased from Byk-Gardner USA, 9104 Guilfod Road, Columbia, Md. at 3 angles: 15°, 45° and 110°. Sparkle values were measured at two angles: 15° and 45°. Flop values were produced based lightness data of the color values according to the aforementioned Formula (II).

Sparkle data of the target coating, differences in color data, flop data and sparkle data are listed in Table 1. The total match metrics (TMM1-TMM3) for each of the specimen coatings were produced using 3 different formulas.

Each of the TMM1 was produced according to a linear function:

$$\mathrm{TMM1}=X_1+X_2+X_3+X_4+X_5+X_6$$

wherein:
$X_1=((\Delta E_{15})^{0.5})/3$
$X_2=((\Delta E_{45})^{0.75})/2$
$X_3=(\Delta E_{110})/2$
$X_4=((3|(\Delta f-0.0575)|)^4)/10$, when $\Delta f \geq 0$
$X_4=((3|(-\Delta f+0.0575)|)^4)/10$, when $\Delta f < 0$
$X_5=(|\Delta S_{15}|)^2/S'_{15}$, when $\Delta S_{P1} \geq 0$
$X_5=1.5(|\Delta S_{15}|)^2/S'_{15}$, when $\Delta S_{15} < 0$
$X_6=1.5(|\Delta S_{45}|)^2/S'_{45}$, when $\Delta S_{45} \geq 0$
$X_6=2.25(|\Delta S_{45}|)^2/S'_{45}$, when $\Delta S_{45} < 0$.

Each of TMM2 was produced according to a weighted linear function:

$$\mathrm{TMM2}=0.5(X'_1+X'_2+X'_3+X'_4+X'_5+X'_6)$$

wherein:
$X'_1=0.5(\Delta E_{15})$
$X'_2=0.75(\Delta E_{45})$
$X'_3=\Delta E_{110}$
$X'_4=((3|(\Delta f)|)^4)/10$ $X'_5 = |\Delta S_{15}|/S^t_{15}$ $X'_6 = |\Delta S_{45}|/S^t_{45}$.

Each of TMM3 was produced according to a non-linear function:

$$TMM3 = 0.8(0.15(X''_1 + 12(X''_5)^{0.75} + (0.5(X''_2 + 12(X''_6))^{1.25} + 0.65(X''_3)^{1.75} + X''_4)$$

wherein:

$X''_1 = \Delta E_{15}$ $X''_2 = \Delta E_{45}$ $X''_3 = \Delta E_{110}$ $X''_4 = ((3|(\Delta f)|)^4/10$ $X''_5 = |\Delta S_{15}|/S^t_{15}$ $X''_6 = |\Delta S_{45}|/S^t_{45}$.

The specimen coating were ranked based on their TMM values. The specimen 3 was ranked No. 1 with all three TMM values (Table 2).

TABLE 1

Coating data and Total Matching Metrics.

|  | Target Coating | Specimen 1 (S1) | Specimen 2 (S2) | Specimen 3 (S3) |
|---|---|---|---|---|
| $S^t_{15}$ | 3.55 | | | |
| $S^t_{45}$ | 2.01 | | | |
| $\Delta E_{15}$ | | 7.05 | 4.49 | 3.15 |
| $\Delta E_{45}$ | | 1.26 | 1.47 | 0.44 |
| $\Delta E_{110}$ | | 1.69 | 1.48 | 1.34 |
| $\Delta f$ | | −0.14 | 0.04 | 0.04 |
| $\Delta S_{15}$ | | 2.04 | 1.51 | 1.87 |
| $\Delta S_{45}$ | | 0.19 | 0.1 | 0.19 |
| TMM 1 | | 3.5 | 2.8 | 2.5 |
| TMM 2 | | 3.42 | 2.65 | 1.94 |
| TMM 3 | | 3.34 | 2.64 | 2.26 |

TABLE 2

Ranking of specimen coatings based on TMMs.

|  | TMM 1 | TMM 2 | TMM 3 |
|---|---|---|---|
| S 1 | 3 | 3 | 3 |
| S 2 | 2 | 2 | 2 |
| S 3 | 1 | 1 | 1 |

Note:
"1" being the best match to the target coating.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the invention as set forth in the appended claims and their legal equivalents.

What is claimed is:

1. A process for producing a total match metric for matching color and appearance of a target coating and at least a specimen coating, the process comprising the steps of:

A0) measuring a specimen color data and a specimen sparkle data from a specimen coating having a specimen coating composition, and saving said specimen color data and specimen sparkle data with a specimen coating formulation in a color database;

A1) obtaining target color data of the target coating and said specimen color data of the specimen coating produced from the specimen coating composition, wherein the target color data comprise target color values measured at three or more color viewing angles and the specimen color data comprise specimen color data values measured at the three or more color viewing angles, and wherein the specimen color data is obtained from the color database;

A2) producing color difference values (ΔE) at each of the color viewing angles based on the target color data and the specimen color data values at each of the color viewing angles;

A3) obtaining target sparkle data of the target coating and said specimen sparkle data of the specimen coating, wherein the target sparkle data comprise target sparkle values measured at one or more sparkle viewing angles and the specimen sparkle data comprise specimen sparkle values measured at the one or more sparkle viewing angles, and wherein the specimen sparkle data is obtained from the color database;

A4) producing sparkle difference values (ΔS) at each of the sparkle viewing angles based on the target sparkle data and the specimen sparkle data at each of the sparkle viewing angles;

A5) generating target flop data ($f^t$) of the target coating based on target lightness value derived from the target color data and specimen flop data ($f^s$) of the specimen coating based on a specimen lightness value derived from the specimen color data;

A6) producing a flop difference value (Δf) based on the target flop data and the specimen flop data; and A7) producing the total match metric (TMM) of the target coating and the specimen coating based on the color difference values (ΔE), the sparkle difference values (ΔS) and the flop difference value (Δf).

2. The process of claim 1, wherein the total match metric (TMM) is produced according to Formula (I):

$$TMM = f[\Delta E_{A1}, \Delta E_{A2}, \Delta E_{A3}, \Delta f, \Delta S_{P1}, \Delta S_{P2}] \quad (I);$$

wherein, $\Delta E_{A1}$ is a color difference value at color viewing angle $A_1$, $\Delta E_{A2}$ is a color difference value at color viewing angle $A_2$, $\Delta E_{A3}$ is a color difference value at color viewing angle $A_3$, Δf is the flop difference value based on the target flop data ($f^t$) and the specimen flop data ($f^s$);

$\Delta S_{P1}$ is a sparkle difference value at sparkle viewing angle $P_1$, $\Delta S_{P2}$ is a sparkle difference value at sparkle viewing angle $P_2$;

the target flop data ($f^t$) is produced according to Formula (II-a):

$$f^t = g(L^t_{A1} - L^t_{A3})^{g'}/(L^t_{A2})^{g''} \quad (II\text{-}a);$$

the specimen flop data ($f^s$) is produced according to Formula (II-b):

$$f^s = g(L^s_{A1} - L^s_{A3})^{g'}/(L^s_{A2})^{g''} \quad (II\text{-}b);$$

g is a number in a range of from about 1 to about 6,
g' is a number in a range of from about 1 to about 3, and
g" is a number in a range of from about 0.1 to about 2,
$L^t_{A1}$ is the target lightness value derived from the target color data at the color viewing angle $A_1$,
$L^t_{A2}$ is the target lightness value derived from the target color data at the color viewing angle $A_2$,
$L^t_{A3}$ is the target lightness value derived from the target color data at the color viewing angle $A_3$,
$L^s_{A1}$ is the specimen lightness value derived from the specimen color data at the color viewing angle $A_1$,
$L^s_{A2}$ is the specimen lightness value derived from the specimen color data at the color viewing angle $A_2$,
$L^s_{A3}$ is the specimen lightness value derived from the specimen color data at the color viewing angle $A_3$;
the flop difference value ($\Delta f$) is produced according to Formula (III), (IV) or (V):

$$\Delta f = (f^s - f^t)/f^t, \text{ when } f^t < z \quad (III)$$

$$\Delta f = (f^s - z)/z, \text{ when } f^s \geq z \text{ and } f^t < z \quad (IV)$$

$$\Delta f = 0, \text{ when } f^s \geq z \text{ and } f^t \geq z \quad (V),$$

z is a number in a range of from about 12 to about 20;
the sparkle difference values are produced according to Formula (VI) and (VII):

$$\Delta S_{P1} = f(S^t_{P1}, S^s_{P1}) \quad (VI)$$

$$\Delta S_{P2} = f(S^t_{P2}, S^s_{P2}) \quad (VII),$$

$S^t_{P1}$ is the target sparkle data at the sparkle viewing angle $P_1$,
$S^s_{P1}$ is the specimen sparkle data at the sparkle viewing angle $P_1$,
$S^t_{P2}$ is the target sparkle data at the sparkle viewing angle $P_2$, and
$S^s_{P2}$ is the specimen sparkle data at the sparkle viewing angle $P_2$;
wherein the color viewing angles are aspecular angles $A_1$ in a range of from about 5° to about 25°, $A_2$ in a range of from about 30° to about 90° and $A_3$ in a range of from about 95° to about 165°; and the sparkle viewing angles are aspecular angles $P_1$ in a range of from about 5° to about 25° and $P_2$ in a range of from about 30° to about 90°.

3. The process of claim 2, wherein the Formula (I) is:

$$TMM = X_1 + X_2 + X_3 + X_4 + X_5 + X_6 \quad (I\text{-}a),$$

wherein,
$X_1 = ((\Delta E_{A1})^n)/m$, n is a number in a range of from about 0.1 to about 2, m is a number in a range of from about 1 to about 5;
$X_2 = ((\Delta E_{A2})^{n'})/m'$, n' is a number in a range of from about 0.1 to about 2, m' is a number in a range of from about 1 to about 5;
$X_3 = (\Delta E_{A3})^{n''}/m''$, n" is a number in a range of from 0.1 to 2, m" is a number in a range of from about 1 to about 5;
$X_4 = ((a|(\Delta f - b)|)^q)/p$, when $\Delta f \geq 0$; or $X_4 = ((a|(-\Delta f + b)|)^q)/p$, when $\Delta f < 0$, a is a number in a range of from about 1 to about 5, b is a number in a range of from about 0.001 to about 0.1, p is a number in a range of from about 2 to about 20, q is a number in a range of from about 1 to about 5;
$X_5 = (|\Delta S_{P1}|)^r/S^t_{P1}$, when $\Delta S_{P1} \geq 0$; or $X_5 = c(|\Delta S_{P1}|)^r/S^t_{P1}$, when $\Delta S_{P1} < 0$; $S^t_{P1}$ is the target sparkle data at the sparkle viewing angle $P_1$, r is a number in a range of from about 1 to about 3, c is a number in a range of from about 1.1 to about 6; and
$X_6 = d(|\Delta S_{P2}|)^{r'}/S^t_{P2}$, when $\Delta S_{P2} \geq 0$; or $X_6 = d'(|\Delta S_{P2}|)^{r'}/S^t_{P2}$, when $\Delta S_{P2} < 0$; $S^t_{P2}$ is the target sparkle data at the sparkle viewing angle $P_2$, r' is a number in a range of from about 1 to about 3, d is a number in range of from about 1.10 to about 6, d' is a number in a range of from about 1.11 to about 8, and d'>d.

4. The process of claim 2, wherein the Formula (I) is:

$$TMM = k(X'_1 + X'_2 + X'_3 + X'_4 + X'_5 + X'_6) \quad (I\text{-}b),$$

wherein:
k is a predetermined constant,
$X'_1 = \alpha(\Delta E_{A1})$, $\alpha$ is a number in a range of from about 0.1 to about 6,
$X'_2 = \beta(\Delta E_{A2})$, $\beta$ is a number in a range of from about 0.1 to about 6,
$X'_3 = \gamma(\Delta E_{A3})$, $\gamma$ is a number in a range of from about 0.1 to about 6,
$X'_4 = ((\lambda|(\Delta f)|)^\epsilon)/10$, $\lambda$ is a number in a range of from about 1 to about 6, $\epsilon$ is a number in a range of from about 1 to about 6,
$X'_5 = |\Delta S_{P1}|/S^t_{P1}$, and
$X'_6 = |\Delta S_{P2}|/S^t_{P2}$.

5. The process of claim 2, wherein the Formula (I) is:

$$TMM = k_1(k_2(X''_1 + k_3(X''_5)^{y_1})^{y_1} + (k_4(X''_2 + k_5(X''_6))^{y_2})^{y_2} + k_6(X''_3)^{y_3} + X''_4) \quad (I\text{-}c),$$

wherein:
$k_1$ is a number in a range of from about 0.1 to about 6,
$k_2$ is a number in a range of from about 0.1 to about 3,
$k_3$ is a number in a range of from about 1 to about 20,
$k_4$ is a number in a range of from about 0.1 to about 3,
$k_5$ is a number in a range of from about 0.1 to about 3,
$k_6$ is a number in a range of from about 0.1 to about 3,
$y_1$ is a number in a range of from about 0.1 to about 3,
$y_2$ is a number in a range of from about 1 to about 6,
$y_3$ is a number in a range of from about 1 to about 6,
$X''_1 = \alpha(\Delta E_{A1})$, $\alpha$ is a number in a range of from about 0.1 to about 6,
$X''_2 = \beta(\Delta E_{A2})$, $\beta$ is a number in a range of from about 0.1 to about 6,
$X''_3 = \gamma(\Delta E_{A3})$, $\gamma$ is a number in a range of from about 0.1 to about 6,
$X''_4 = ((\lambda|(\Delta f)|)^\epsilon)/10$, $\lambda$ is a number in a range of from about 1 to about 6, $\epsilon$ is a number in a range of from about 1 to about 6,
$X''_5 = |\Delta S_{P1}|/S^t_{P1}$, and
$X''_6 = |\Delta S_{P2}|/S^t_{P2}$.

6. The process of claim 1 further comprising the steps of:
A8) producing at least a target image of the target coating, the target image comprises target display R,G,B values based on the target color data, the target sparkle data and the target flop data;
A9) producing at least a specimen image of the specimen coating, the specimen image comprises specimen display R,G,B values based on the specimen color data, the specimen sparkle data and the specimen flop data;
A10) displaying the target image, the specimen image, or a combination thereof, on a display device based on the target display R,G,B values and the specimen display R,G,B values.

7. The process of claim 1 further comprising the steps of:
A11) producing a matching coating composition for matching color and appearance of the target coating, wherein the matching coating composition is based on the specimen coating composition when the total match metric (TMM) is within a predetermined matching tolerance range for matching the target coating and the specimen coating, and optionally producing a matching coating matching color and appearance of the target coating using the matching coating composition.

8. The process of claim 1 further comprising the steps of:

A12) producing at least one modified coating formulation based on the total match metric (TMM) for a modified coating, when the total match metric (TMM) is outside a predetermined matching tolerance range for match the target coating and the specimen coating;

A13) producing the modified coating based on the modified coating formulation;

A14) repeating the steps A1)-A7) to produce a modified total match metric of the target coating and the modified coating;

A15) repeating the steps A12)-A15) until the modified total match metric is within the predetermined matching tolerance range;

A16) optionally, producing a matching coating composition for matching color and appearance of the target coating, wherein the matching coating composition is based on the modified coating formulation having the modified total match metric within the predetermined matching tolerance range; and A17) optionally, producing a matching coating matching color and appearance of the target coating using the matching coating composition.

9. The process of claim 1, wherein the target coating is coated over a substrate.

10. The process of claim 9, wherein the substrate is a vehicle, a vehicle part, or a combination thereof.

11. A process for producing a matching coating for matching color and appearance of a target coating coated over a substrate, the process comprising the steps of:

B1) obtaining target coating identification data, target color data, target sparkle data and target flop data of the target coating, wherein the target color data comprise target color values measured at three or more color viewing angles, the target sparkle data comprise target sparkle values measured at one or more sparkle viewing angles, and the target flop data is generated based on target lightness value derived from the target color data;

B2) retrieving at least a specimen coating formulation from a color database based on the target coating identification data, the color database comprise coating formulations interrelated to and retrievable based on coating identification data;

B3) obtaining specimen color data, specimen sparkle data and specimen flop data associated with the specimen coating formulation, the specimen color data comprise specimen color data values measured at the three or more color viewing angles, the specimen sparkle data comprise specimen sparkle values measured at the one or more sparkle viewing angles, and the specimen flop data is generated based on a specimen lightness value derived from the specimen color data, wherein:

the specimen color data, specimen sparkle data and the specimen flop data are obtained by: (a) measuring at least one of the specimen color data and specimen sparkle data from a specimen coating produced based on the specimen coating formulation and generating the specimen flop data based on the specimen color data, (b) retrieving at least one of the specimen color data, specimen sparkle data and the specimen flop data associated with the specimen coating formulation from the color database, or (c) a combination of (a) and (b);

B4) producing color difference values ($\Delta E$) at each of the color viewing angles based on the target color data and the specimen color data values at each of the color viewing angles;

B5) producing sparkle difference values ($\Delta S$) at each of the sparkle viewing angles based on the target sparkle data and the specimen sparkle data at each of the sparkle viewing angles;

B6) producing a flop difference value ($\Delta f$) based on the target flop data and the specimen flop data; and B7) producing a total match metric (TMM) of the target coating and the specimen coating based on the color difference values ($\Delta E$), the sparkle difference values ($\Delta S$) and the flop difference value ($\Delta f$).

12. The process of claim 11, wherein the total match metric (TMM) is produced according to Formula (I):

$$TMM = f[\Delta E_{A1}, \Delta E_{A2}, \Delta E_{A3}, \Delta f, \Delta S_{P1}, \Delta S_{P2}] \quad (I);$$

wherein, $\Delta E_{A1}$ is a color difference value at color viewing angle $A_1$, $\Delta E_{A2}$ is a color difference value at color viewing angle $A_2$, $\Delta E_{A3}$ is a color difference value at color viewing angle $A_3$, $\Delta f$ is the flop difference value based on the target flop data ($f^t$) and the specimen flop data ($f^s$);

$\Delta S_{P1}$ is a sparkle difference value at sparkle viewing angle $P_1$, $\Delta S_{P2}$ is a sparkle difference value at sparkle viewing angle $P_2$;

the target flop data ($f^t$) is produced according to Formula (II-a):

$$f^t = g(L^t_{A1} - L^t_{A3})^{g'}/(L^t_{A2})^{g''} \quad (II-a);$$

the specimen flop data ($f^s$) is produced according to Formula (II-b):

$$f^s = g(L^s_{A1} - L^s_{A3})^{g'}/(L^s_{A2})^{g''} \quad (II-b);$$

g is a number in a range of from about 1 to about 6, g' is a number in arrange of from about 1 to about 3, and g'' is a number in a range of from about 0.1 to about 2, $L^t_{A1}$ is the target lightness value derived from the target color data at the color viewing angle $A_1$, $L^t_{A2}$ is the target lightness value derived from the target color data at the color viewing angle $A_2$, $L^t_{A3}$ is the target lightness value derived from the target color data at the color viewing angle $A_3$, $L^s_{A1}$ is the specimen lightness value derived from the specimen color data at the color viewing angle $A_1$, $L^s_{A2}$ is the specimen lightness value derived from the specimen color data at the color viewing angle $A_2$, $L^s_{A3}$ is the specimen lightness value derived from the specimen color data at the color viewing angle $A_3$;

the flop difference value ($\Delta f$) is produced according to Formula (III), (IV) or (V):

$$\Delta f = (f^s - f^t)/f^t, \text{ when } f^t < z \quad (III)$$

$$\Delta f = (f^s - z)/z, \text{ when } f^t \geq z \text{ and } f^s < z \quad (IV)$$

$$\Delta f = 0, \text{ when } f^t \geq z \text{ and } f^s \geq z \quad (V),$$

z is a number in a range of from about 12 to about 20;

the sparkle difference values are produced according to Formula (VI) and (VII):

$$\Delta S_{P1} = f(S^t_{P1}, S^s_{P1}) \quad (VI)$$

$$\Delta S_{P2} = f(S^t_{P2}, S^s_{P2}) \quad (VII),$$

$S^t_{P1}$ is the target sparkle data at the sparkle viewing angle $P_1$,
$S^s_{P1}$ is the specimen sparkle data at the sparkle viewing angle $P_1$,
$S^t_{P2}$ is the target sparkle data at the sparkle viewing angle $P_2$, and
$S^s_{P2}$ is the specimen sparkle data at the sparkle viewing angle $P_2$;

wherein the color viewing angles are aspecular angles $A_1$ in a range of from about 5° to about 25°, $A_2$ in a range of from about 30° to about 90° and $A_3$ in a range of from about 95° to about 165°; and the sparkle viewing angles are aspecular angles $P_1$ in a range of from about 5° to about 25° and $P_2$ in a range of from about 30° to about 90°.

13. The process of claim 12, wherein the Formula (I) is:

$$TMM = X_1 + X_2 + X_3 + X_4 + X_5 + X_6 \quad (I\text{-}a),$$

wherein,
$X_1 = ((\Delta E_{A1})^n)/m$, n is a number in a range of from about 0.1 to about 2, m is a number in a range of from about 1 to about 5;
$X_2 = ((\Delta E_{A2})^{n'})/m'$, n' is a number in a range of from about 0.1 to about 2, m' is a number in a range of from about 1 to about 5;
$X_3 = (\Delta E_{A3})^{n''}/m''$, n'' is a number in a range of from about 0.1 to about 2, m'' is a number in a range of from about 1 to about 5;
$X_4 = ((a|(\Delta f - b)|)^q)/p$, when $\Delta f \geq 0$; or $X_4 = ((a|(-\Delta f + b)|)^q/p$, when $\Delta f < 0$, a is a number in a range of from about 1 to about 5, b is a number in a range of from about 0.001 to about 0.1, p is a number in a range of from about 2 to about 20, q is a number in a range of from about 1 to about 5;
$X_5 = (|\Delta S_{P1}|)^r/S^t_{P1}$, when $\Delta S_{P1} \geq 0$; or $X_5 = c(|\Delta S_{P1}|)^r/S^t_{P1}$, when $\Delta S_{P1} < 0$; $S^t_{P1}$ is the target sparkle data at the sparkle viewing angle $P_1$, r is a number in a range of from about 1 to about 3, c is a number in a range of from about 1.1 to about 6; and
$X_6 = d(|\Delta S_{P2}|)^{r'}/S^t_{P2}$, when $\Delta S_{P2} \geq 0$; or $X_6 = d'(|S_{P2}|)^{r'}/S^t_{P2}$, when $\Delta S_{P2} < 0$; $S^t_{P2}$ is the target sparkle data at the sparkle viewing angle $P_2$, r' is a number in a range of from about 1 to about 3, d is a number in range of from about 1.10 to about 6, d' is a number in a range of from about 1.11 to about 8, and d' > d.

14. The process of claim 12, wherein the Formula (I) is:

$$TMM = k(X'_1 + X'_2 + X'_3 + X'_4 + X'_5 + X'_6) \quad (I\text{-}b),$$

wherein:
k is a predetermined constant,
$X'_1 = \alpha(\Delta E_{A1})$, $\alpha$ is a number in a range of from about 0.1 to about 6,
$X'_2 = \beta(\Delta E_{A2})$, $\beta$ is a number in a range of from about 0.1 to about 6,
$X'_3 = \gamma(\Delta E_{A3})$, $\gamma$ is a number in a range of from about 0.1 to about 6,
$X'_4 = ((\lambda|(\Delta f)|)^\epsilon/10$, $\lambda$ is a number in a range of from about 1 to about 6, $\epsilon$ is a number in a range of from about 1 to about 6,
$X'_5 = |\Delta S_{P1}|/S^t_{P1}$, and
$X'_6 = |\Delta S_{P2}|/S^t_{P2}$.

15. The process of claim 12, wherein the Formula (I) is:

$$TMM = k_1(k_2(X''_1 + k_3(X''_5)^{y_1} + (k_4(X''_2 + k_5(X''_6)^{y_2} + k_6(X''_3)^{y_3} + X''_4) \quad (I\text{-}c),$$

wherein:
$k_1$ is a number in a range of from about 0.1 to about 6,
$k_2$ is a number in a range of from about 0.1 to about 3,
$k_3$ is a number in a range of from about 1 to about 20,
$k_4$ is a number in a range of from about 0.1 to about 3,
$k_5$ is a number in a range of from about 0.1 to about 3,
$k_6$ is a number in a range of from about 0.1 to about 3,
$y_1$ is a number in a range of from about 0.1 to about 3,
$y_2$ is a number in a range of from about 1 to about 6,
$y_3$ is a number in a range of from about 1 to about 6,
$X''_1 = \alpha(\Delta E_{A1})$, $\alpha$ is a number in a range of from about 0.1 to about 6,
$X''_2 = \beta(\Delta E_{A2})$, $\beta$ is a number in a range of from about 0.1 to about 6,
$X''_3 = \gamma(\Delta E_{A3})$, $\gamma$ is a number in a range of from about 0.1 to about 6,
$X''_4 = ((\lambda|(\Delta f)|)^\epsilon/10$, $\lambda$ is a number in a range of from about 1 to about 6, $\epsilon$ is a number in a range of from about 1 to about 6,
$X''_5 = |\Delta S_{P1}|/S^t_{P1}$, and
$X''_6 = |\Delta S_{P2}|/S^t_{P2}$.

16. The process of claim 11 further comprising the steps of:
B8) producing at least a target image of the target coating, the target image comprises target display R,G,B values based on the target color data, the target sparkle data and the target flop data;
B9) producing at least a specimen image of the specimen coating, the specimen image comprises specimen display R,G,B values based on the specimen color data, the specimen sparkle data and the specimen flop data;
B10) displaying the target image, the specimen image, or a combination thereof, on a display device based on the target display R,G,B values and the specimen display R,G,B values.

17. The process of claim 11 further comprising the steps of:
B11) producing a matching coating composition for matching color and appearance of the target coating, wherein the matching coating composition is based on a specimen coating composition when the total match metric (TMM) is within a predetermined matching tolerance range for matching the target coating and the specimen coating, and optionally producing the matching coating matching color and appearance of the target coating using the matching coating composition.

18. The process of claim 11 further comprising the steps of:
B12) producing at least one modified coating formulation based on the total match metric (TMM) for a modified coating, when the total match metric (TMM) is outside a predetermined matching tolerance range for match the target coating and the specimen coating;
B13) producing the modified coating based on the modified coating formulation;
B14) repeating the steps B3)-B7) to produce a modified total match metric of the target coating and the modified coating;
B15) repeating the steps B12)-B15) until the modified total match metric is within the predetermined matching tolerance range; and
B16) producing a matching coating composition for matching color and appearance of the target coating, wherein the matching coating composition is based on the modified coating formulation having the modified total match metric within the predetermined matching tolerance range; and B17) optionally, producing the matching coating matching color and appearance of the target coating using the matching coating composition.

19. The process of claim 11 wherein the substrate is a vehicle, a vehicle part, or a combination thereof.

20. The process of claim 19, wherein the target coating identification data is selected from a name or a code of the target coating, color values of the target coating measured at one or more viewing angles, a vehicle identification number (VIN) of the vehicle, a part of the VIN, make of the vehicle, model and model year of the vehicle, manufacturing site information of the vehicle, manufacturer's paint code of the vehicle, or a combination thereof.

21. A system for producing a total match metric for matching color and appearance of a target coating and at least a specimen coating, the system comprising:
- C1) a computing program product comprises computer executable codes stored on a computer readable storage medium, the computing program product causes a computing device to perform a computing process when in operation, the computing process comprises the steps of:
  - D1) receiving target coating identification data of the target coating when available, target color values and target sparkle values of the target coating and specimen color data values and specimen sparkle values of the specimen coating;
  - D2) generating target flop data of the target coating based on target lightness value derived from the target color values and specimen flop data of the specimen coating based on specimen lightness value derived from the specimen color data;
  - D3) producing color difference values ($\Delta E$) at each of the color viewing angles based on the target color values and the specimen color data values at each of the color viewing angles;
  - D4) producing sparkle difference values ($\Delta S$) at each of the sparkle viewing angles based on the target sparkle values and the specimen sparkle values at each of the sparkle viewing angles;
  - D5) producing a flop difference value ($\Delta f$) based on the target flop data and the specimen flop data;
  - D6) producing the total match metric (TMM) of the target coating and the specimen coating based on the color difference values ($\Delta E$), the sparkle difference values ($\Delta S$) and the flop difference value ($\Delta f$); and
  - D7) outputting the total match metric as one or more output signals to an output device.

22. The system of claim 21 further comprising:
- C2) a color measuring device for producing the target color values of the target coating at three or more color viewing angles and the specimen color data values of the specimen coating at the three or more color viewing angles;
- C3) a sparkle measuring device for producing the target sparkle values of the target coating at one or more sparkle viewing angles and the specimen sparkle values of the specimen coating at the one or more sparkle viewing angles;
- C4) the computing device functionally in communication with the color measuring device and the sparkle measuring device, when in operation; and
- C5) the output device functionally in communication with the computing device, when in operation.

23. The system of claim 22, wherein the output device is selected from a digital display device, a printer, a digital data storage device, a database, a second computing device, or a combination thereof.

24. The system of claim 21 further comprising:
- C6) a color database functionally in communication with the computing device, the color database comprise coating formulations interrelated to and retrievable based on names or codes of coatings, color characteristics of coatings, appearance characteristics of coatings, vehicle identification numbers (VINs) of vehicles, parts of the VINs, makes of vehicles, models and model years of vehicles, manufacturing sites information of vehicles, manufacturer's paint codes of vehicles, or a combination thereof.

* * * * *